United States Patent
Wang et al.

(10) Patent No.: US 9,440,067 B2
(45) Date of Patent: Sep. 13, 2016

(54) ELECTRODE LEAD AND PACEMAKER USING THE SAME

(75) Inventors: Yu-Quan Wang, Beijing (CN); Li Qian, Beijing (CN); Liang Liu, Beijing (CN); Chen Feng, Beijing (CN); Li Fan, Beijing (CN); Wen-Mei Zhao, Beijing (CN)

(73) Assignees: Tsinghua University, Beijing (CN); HON HAI PRECISION INDUSTRY CO., LTD., New Taipei (TW)

( * ) Notice: Subject to any disclaimer, the term of this patent is extended or adjusted under 35 U.S.C. 154(b) by 323 days.

(21) Appl. No.: 13/527,836

(22) Filed: Jun. 20, 2012

(65) Prior Publication Data

US 2013/0110216 A1 May 2, 2013

(30) Foreign Application Priority Data

Oct. 28, 2011 (CN) .......................... 2011 1 0333521

(51) Int. Cl.
*A61N 1/05* (2006.01)
*A61N 1/362* (2006.01)
*B82Y 30/00* (2011.01)

(52) U.S. Cl.
CPC ................ *A61N 1/056* (2013.01); *A61N 1/05* (2013.01); *A61N 1/0565* (2013.01); *A61N 1/362* (2013.01); *B82Y 30/00* (2013.01)

(58) Field of Classification Search
CPC ...... A61N 1/05; A61N 1/056; A61N 1/0565; A61N 1/0362; A61N 2001/086
USPC ...................... 600/373; 607/119, 5
See application file for complete search history.

(56) References Cited

U.S. PATENT DOCUMENTS

| | | | |
|---|---|---|---|
| 3,893,461 A * | 7/1975 | Preston | 607/17 |
| 5,713,945 A | 2/1998 | Fischer et al. | |
| 7,491,883 B2 * | 2/2009 | Lee et al. | 174/28 |
| 7,493,160 B2 | 2/2009 | Weber et al. | |
| 7,512,447 B2 * | 3/2009 | Marshall et al. | 607/122 |
| 7,596,415 B2 | 9/2009 | Brabec et al. | |
| 2004/0051432 A1 | 3/2004 | Jiang et al. | |
| 2006/0272701 A1 * | 12/2006 | Ajayan et al. | 136/263 |
| 2009/0062895 A1 | 3/2009 | Stahmann et al. | |
| 2009/0194313 A1 | 8/2009 | Jiang et al. | |
| 2009/0255706 A1 | 10/2009 | Jiang et al. | |
| 2010/0147829 A1 | 6/2010 | Liu et al. | |
| 2010/0305504 A1 * | 12/2010 | Wang et al. | 604/114 |
| 2011/0026758 A1 | 2/2011 | Wang et al. | |
| 2011/0160829 A1 | 6/2011 | Foster et al. | |
| 2011/0301657 A1 * | 12/2011 | Walsh et al. | 607/5 |
| 2012/0053649 A1 | 3/2012 | Liu et al. | |
| 2012/0271394 A1 | 10/2012 | Foster et al. | |

FOREIGN PATENT DOCUMENTS

| | | |
|---|---|---|
| CN | 1460638 | 12/2003 |
| CN | 1484275 | 3/2004 |
| CN | 1943805 | 4/2007 |

(Continued)

*Primary Examiner* — William Levicky
(74) *Attorney, Agent, or Firm* — Zhigang Ma (57) ABSTRACT

An electrode lead of a pacemaker includes a metal conductive core and a carbon nanotube film. The metal conductive core defines an extending direction. The carbon nanotube film wraps around the metal conductive core. The carbon nanotube film includes a plurality of carbon nanotubes extending substantially along the extending direction of the metal conductive core. A bared part is defined at one end of the electrode lead. A pacemaker using the above mentioned electrode lead is also disclosed.

20 Claims, 6 Drawing Sheets

(56) References Cited

FOREIGN PATENT DOCUMENTS

| CN | 101499331 | 8/2009 |
|---|---|---|
| CN | 101757723 | 6/2010 |
| CN | 101925379 | 12/2010 |
| CN | 101927057 | 12/2010 |
| CN | 101990147 | 3/2011 |
| TW | 200945372 | 11/2009 |
| TW | 201039670 | 11/2010 |
| TW | I345792 | 7/2011 |

* cited by examiner

ELECTRODE LEAD AND PACEMAKER USING THE SAME

RELATED APPLICATIONS

This application claims all benefits accruing under 35 U.S.C. §119 from China Patent Application No. 201110333521.5, filed on Oct. 28, 2011 in the China Intellectual Property Office, the disclosure of which is incorporated herein by reference.

BACKGROUND

1. Technical Field

The present disclosure relates to an electrode lead based on carbon nanotubes and a pacemaker using the electrode lead.

2. Discussion of Related Art

Pacemakers are electronic therapeutic devices which can be implanted into human bodies. The pacemakers can emit pulse currents to stimulate organs.

The pacemaker includes a pulse generator and an electrode lead. The pulse generator is electrically connected with the electrode lead. The electrode lead includes a connector, an electrode lead, and an electrode tip. The connector is electrically connected with the pulse generator. The connector and the electrode tip are located at two opposite ends of the electrode lead. The electrode lead includes a plurality of metal wires. The connector and the electrode tip are electrically connected with the metal wires. However, the electrode lead composed of the metal wires has poor strength and ductility, and is easily broken due to repeat distortions. Thus, the life of the lead electrode and the pacemaker using the lead electrode are reduced.

What is needed, therefore, is to provide an electrode lead and a pacemaker using the same, which can overcome the shortcomings as discussed above.

BRIEF DESCRIPTION OF THE DRAWINGS

Many aspects of the embodiments can be better understood with references to the following drawings. The components in the drawings are not necessarily drawn to scale, the emphasis instead being placed upon clearly illustrating the principles of the embodiments. Moreover, in the drawings, like reference numerals designate corresponding parts throughout the several views.

DETAILED DESCRIPTION

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Figure 1:
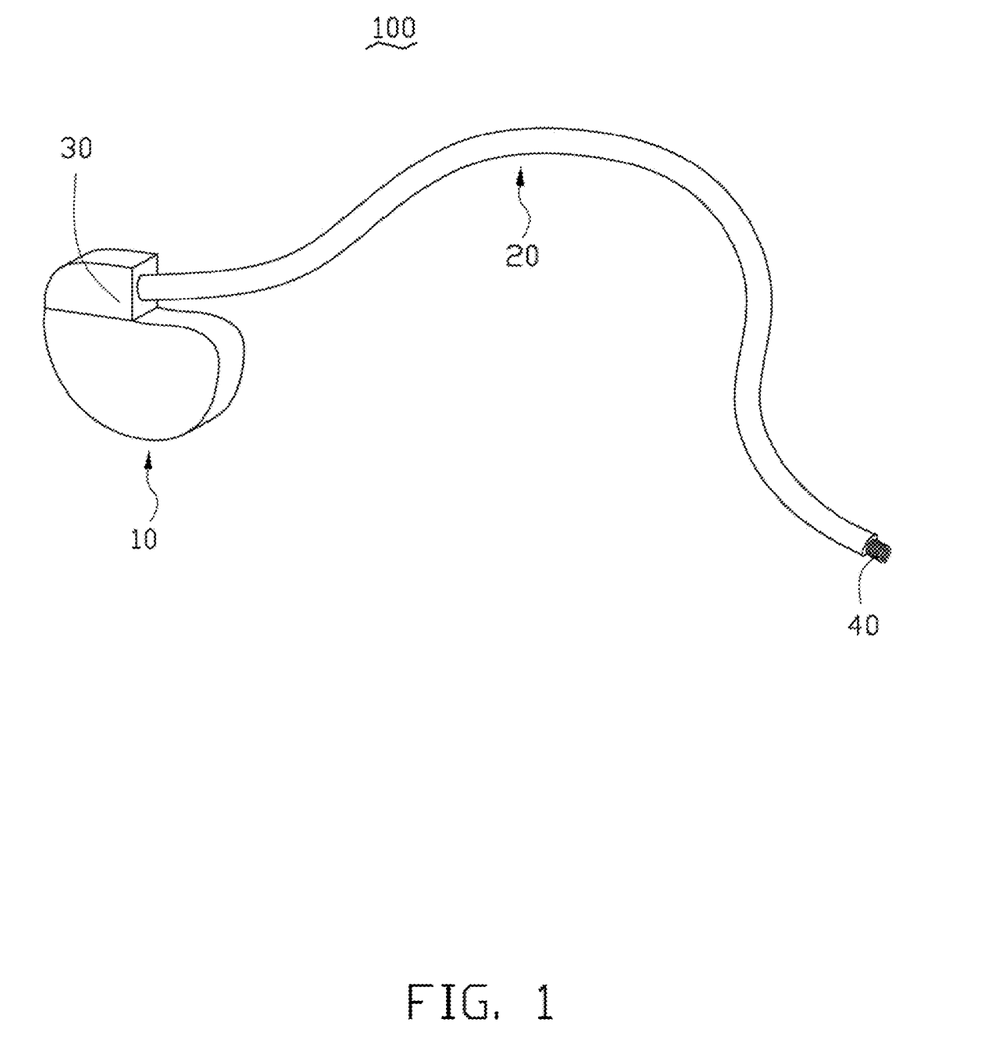
FIG. 1 is a schematic view of one embodiment of a heart pacemaker including an electrode lead.

Referring to FIG. 1, one embodiment of a pacemaker 100 includes a pulse generator 10 and an electrode lead 20 electrically connected with the pulse generator 10. The electrode lead 20 has a connector 30 and a bared part 40 opposite to the connector 30. The electrode lead 20 has a proximal end and a distal end opposite to the proximal end. The connector 30 is located at the proximal end the electrode lead 20, and the bared part 40 is located at the distal end of the electrode lead 20. The electrode lead 20 is electrically connected with the pulse generator 10 through the connector 30. The pulse generator 10 can generate pulse signals to stimulate organs of living beings via the electrode lead 20.

The pulse generator 10 can include a shell (not labeled), a power source (not shown), and a control circuit (not shown). The power source and the control circuit are packaged in the shell. The power source can provide power for the control circuit. Batteries can be used as the power source, such as lithium ion batteries, fuel cells, and physical power batteries. In one embodiment, a lithium-iodine battery is the power source. The control circuit can include an output circuit and a sensing circuit. The output circuit can be used to generate the pulse signals. The sensing circuit can be used to receive electrical signals generated by the stimulated organs and feed these electrical signals back to the output circuit. The output circuit can adaptively adjust to output proper pulse signals according to the feedback of the sensing circuit. The organs can be a heart, brain, or stomach of living beings. In one embodiment, the organ is the heart of a human being. The pulse signals can be a square wave pulsing current. A pulse width of the pulse signals can be in a range from about 0.5 milliseconds to about 0.6 milliseconds. The pulse current can be generated by a charging-discharging process of a capacitor in the control circuit. The shell used for packaging can prevent an interaction between the power source, the control circuit and the living being in which the pacemaker is implanted. A material of the shell can be a metal or alloy, biocompatible, corrosion resistant, and structurally tough or rigid. In one embodiment, the material of the shell is titanium.

Figure 2:
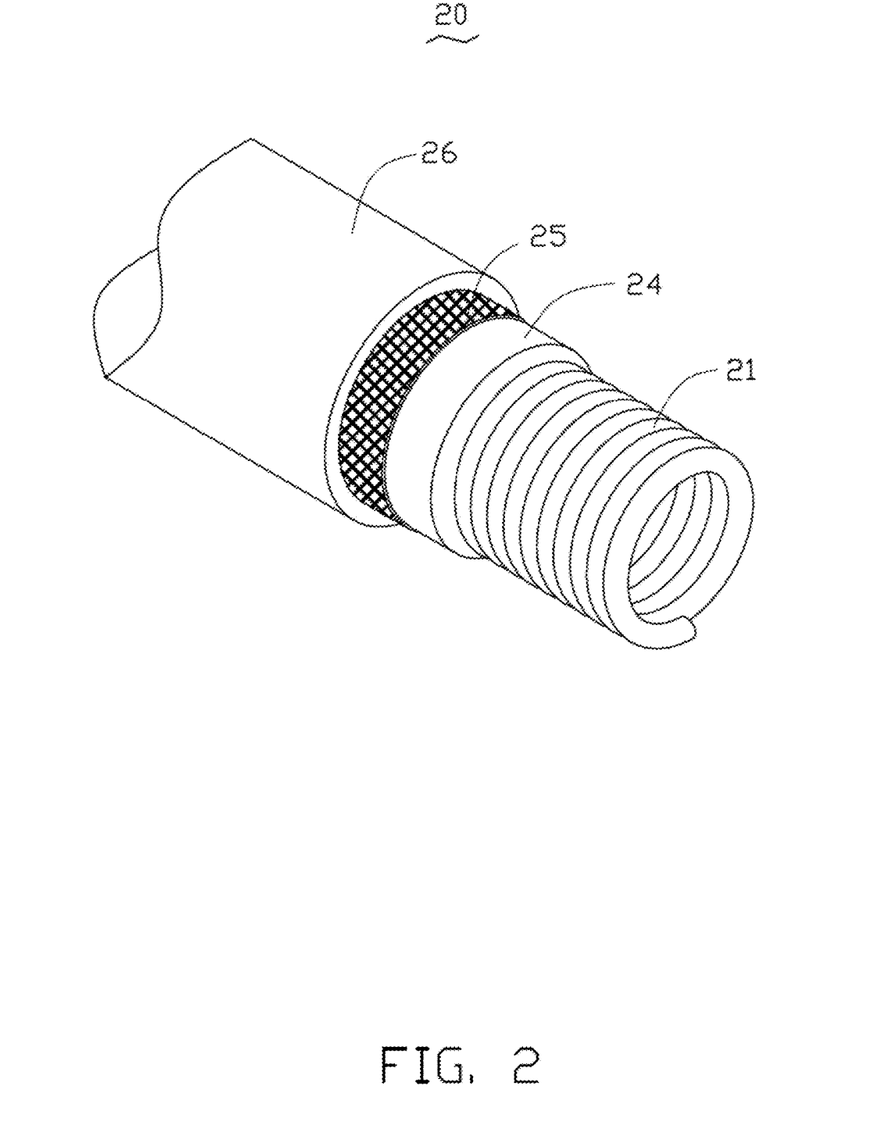
FIG. 2 is a stepped, cross-sectional view of part of the electrode lead shown in FIG. 1.
Figure 3:
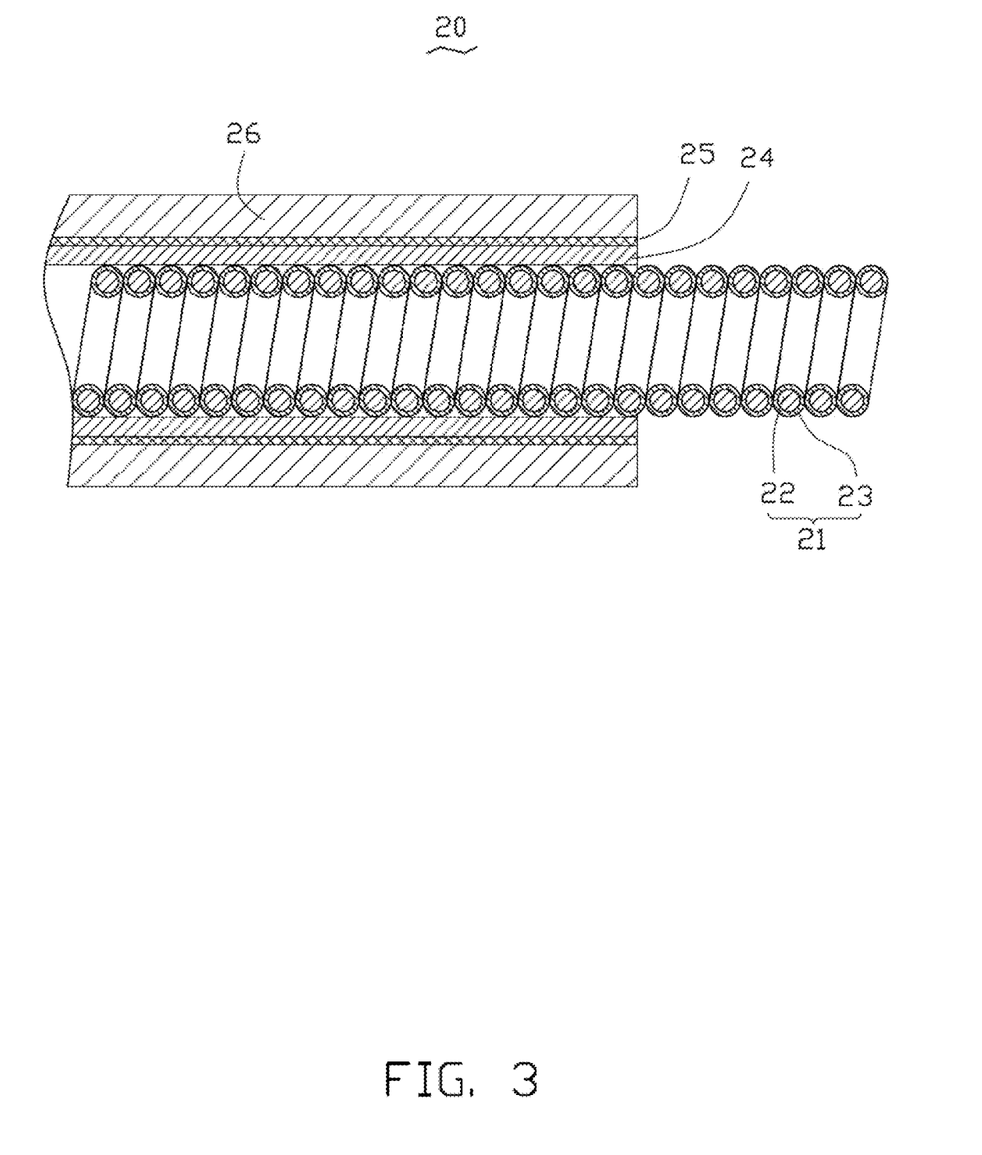
FIG. 3 is a cross-sectional view of part of the electrode lead along an axis of the electrode lead shown in FIG. 1.

Referring FIG. 2 and FIG. 3, the electrode lead 20 can include a conductive structure 21, an insulated layer 24 surrounded the conductive structure 21, a shield layer 25 wrapped around the insulated layer 24, and a coating layer 26 wound around the shield layer 25. In one embodiment, the conductive structure 21 consists of a metal conductive core 22 and a carbon nanotube film 23 wrapped around the metal conductive core 22. The insulated layer 24 surrounds the carbon nanotube film 23. The carbon nanotube film 23 includes a number of carbon nanotubes oriented substantially along a same direction. The carbon nanotubes extend substantially along an axial direction of the metal conductive core 22.

The conductive structure 21 can be a hollow spiral structure with a certain elasticity to improve the lifetime of the electrode lead 20. A diameter of a coil formed by the hollow spiral conductive structure 21 can range from about 4 millimeters to about 6 millimeters. In one embodiment, the diameter of the coil is about 5 millimeters. A thread pitch of the hollow spiral conductive structure 21 can be in a range from about 0 millimeters to about 10 millimeters. The conductive structure 21 can also be a solid structure or a hollow linear structure, and the extending directions of the carbon nanotubes in the carbon nanotube film 23 are substantially parallel to an axial direction of the metal conductive core 22.

The metal conductive core 22 has good electrical conductivity. A material of the metal conductive core 21 can be MP35N®, 35NLT®, stainless steel, carbon fiber, tantalum, titanium, zirconium, niobium, titanium alloy, copper, silver, platinum, platinum-yttrium alloy, or platinum-palladium alloy. MP35N® is an alloy including 35Co—35Ni—20Cr—10Mo, with a weight percentage of titanium being about 1% in the MP35N®. 35NLT® is also an alloy including 35Co—35Ni—20Cr—10Mo with a weigh percentage of titanium being about 0.01% in the 35NLT®. In one embodiment, the material of the metal conductive core 22 is platinum.

The bared part 40 is an exposed part of the conductive structure 21 exposed from the electrode lead 20, and is located at the distal end of the conductive structure 21. That is, the bared part 40 is exposed from the insulated layer 24 to the coating layer 26. The bared part 40 is a part of the metal conductive core 22 and a part of the carbon nanotube film 23 wrapped around the part of the metal conductive core 22. The shape and the structure of the bared part 40 can be the same as the shape and the structure of the conductive structure 21. In one embodiment, the bared part 40 is spiral. A length of the bared part 40 can range from about 0.5 millimeters to about 2 millimeters. The bared part 40 acts as an electrode head of the electrode lead 20. In use, the bared part 40 contacts living cells and carries pulse current signals generated from the pulse generator 10 to the cells. The bared part 40 acts as both stimulating electrode and the sensing electrode. The bared part 40 can be fixed to an organ and tissue to prevent the electrode lead 20 from sliding or falling off the organ and tissue.

Figure 4:
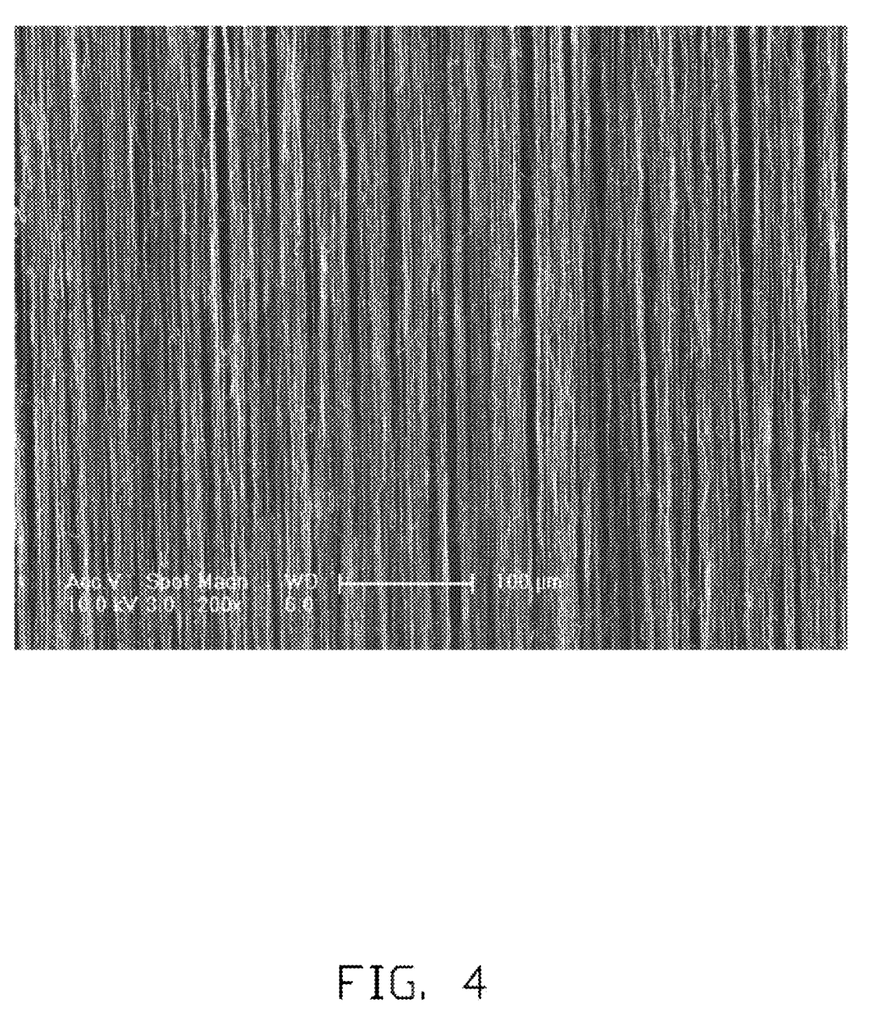
FIG. 4 shows a scanning electronic microscope (SEM) image of a carbon nanotube film used in FIG. 2.

Referring to FIG. 4, the carbon nanotube film 23 is a free-standing film. The carbon nanotube film 23 includes a plurality of carbon nanotubes that can be arranged substantially parallel to a surface of the carbon nanotube film. A large number of the carbon nanotubes in the carbon nanotube film can be oriented along a preferred orientation, meaning that a large number of the carbon nanotubes in the carbon nanotube film are arranged substantially along a same direction. In the carbon nanotube film, an end of one carbon nanotube is joined to another end of an adjacent carbon nanotube arranged substantially along the same direction by van der Waals attractive force. A small number of the carbon nanotubes are randomly arranged in the carbon nanotube film, and has a small if not negligible effect on the larger number of the carbon nanotubes in the carbon nanotube film arranged substantially along the same direction. The carbon nanotubes oriented substantially along the same direction may not be perfectly aligned in a straight line, and some curve portions may exist. Some carbon nanotubes located substantially side by side in contact with each other cannot be excluded.

Figure 5:
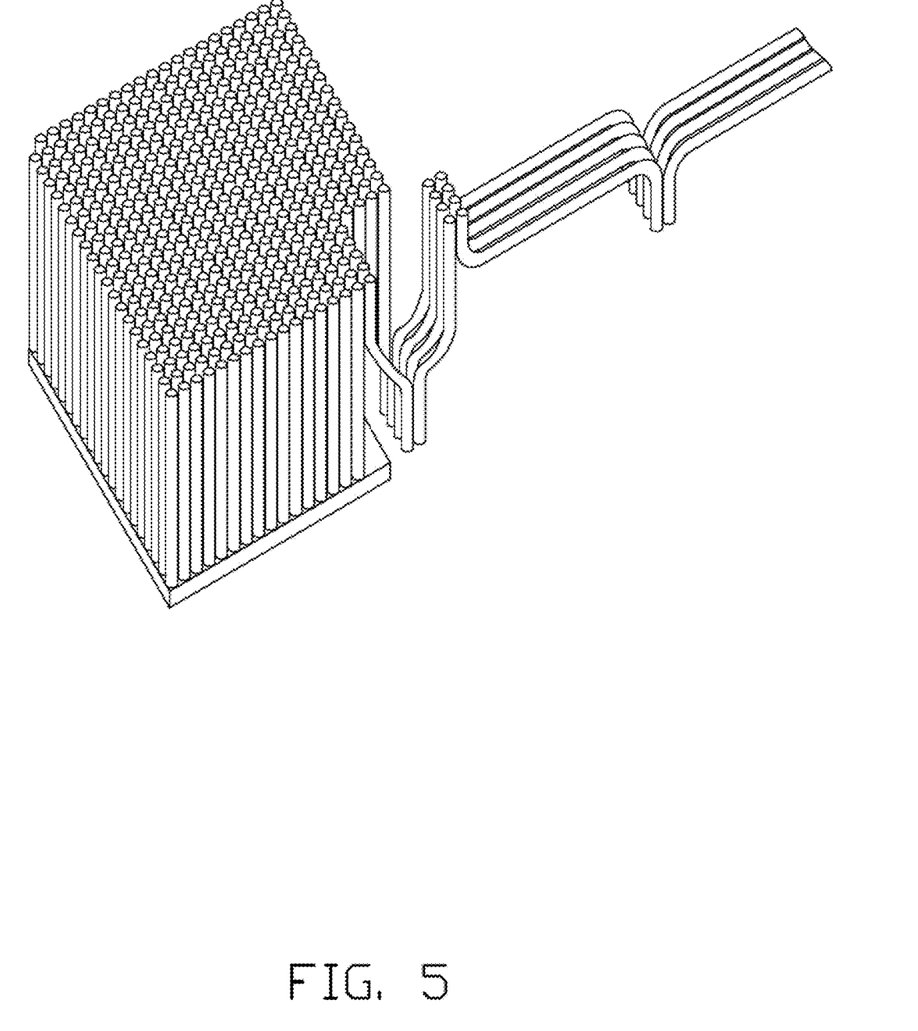
FIG. 5 shows a process schematic view for making the carbon nanotube film shown in FIG. 4 from a carbon nanotube array.

Referring to FIG. 5, a method for making the carbon nanotube film 23 can include:

S1, providing a carbon nanotube array; and

S2, selecting a carbon nanotube segment from the carbon nanotube array using a tool, and drawing the carbon nanotube segment at a predetermined speed, thereby pulling out a continuous carbon nanotube drawn film including a plurality of carbon nanotube segments joined end-to-end by van der Waals attractive force therebetween.

In step S1, the carbon nanotube array is formed on a substrate. The carbon nanotube array consists of carbon nanotubes. The carbon nanotubes can be single-wall carbon nanotubes, double-wall carbon nanotubes, multi-wall carbon nanotubes, or any combinations thereof. Diameters of the carbon nanotubes can be from about 0.5 nanometers to about 50 nanometers. Lengths of the carbon nanotubes can be from about 50 nanometers to about 5 millimeters. In one embodiment, the lengths of the carbon nanotubes can be from about 100 micrometers to about 900 micrometers. In one embodiment, the carbon nanotubes are multi-wall carbon nanotubes, and the carbon nanotubes are substantially parallel to each other and substantially perpendicular to the substrate. The carbon nanotube array is essentially free of impurities, such as carbonaceous or residual catalyst particles. The carbon nanotube array can be a super aligned carbon nanotube array. A method for making the carbon nanotube array is unrestricted, and can be by chemical vapor deposition methods or other methods.

In step S2, the pulling direction can be substantially perpendicular to the growing direction of the carbon nanotube array. During the pulling process, as the initial carbon nanotube segments are drawn out, other carbon nanotube segments are also drawn out end to end due to van der Waals force between ends of adjacent segments. This process of pulling produces a substantially continuous and uniform carbon nanotube film having a predetermined width.

A method for making the conductive structure 21 is also provided. Firstly, a carbon nanotube film drawn from a carbon nanotube array is provided. One end of the carbon nanotube film is adhered to an outer surface of the metal conductive core 22, and the carbon nanotubes in the carbon nanotube film substantially extend along the axial direction of the metal conductive core 22. The carbon nanotube film or the metal conductive core 22 is rotated to wind the carbon nanotube film around the outer surface of the metal conductive core 22. The carbon nanotube film can be adhered to the metal conductive core 22 by van der Waals force because the carbon nanotube film has a large surface. In one embodiment, an adhesive layer is coated on the metal conductive core 22, and the carbon nanotube film is adhered to the metal conductive core 22 by the adhesive layer.

Secondly, a hollow spiral conductive structure 21 is formed by twisting the metal conductive core 22 with the carbon nanotube film. In one embodiment, the metal conductive core 22 with the carbon nanotube film is spirally twisted around a linear supporter, and then the linear supporter is removed to form the hollow spiral conductive structure 21.

A material of the insulated layer 24 can be silicone, polyurethane, polytetrafluoroethylene, silicone-polyurethane copolymer, polyethylene, polypropylene, polystyrene, polystyrene foam, or nanoclay-polymer composite material. The polymer material in the nanoclay-polymer composite material can be silicone, polyurethane, or polyolefin such as polyethylene or polypropylene. In one embodiment, the insulated layer 24 is made of polystyrene foam. The material of the insulated layer 24 is not limited, as long as the insulated layer 24 can function as an electrical insulator.

The shield layer 25 is used to shield electromagnetic interference or outer signals interference. A material of the shield layer 25 can be an electrical conductive material, such as metal or carbon nanotubes. In one embodiment, the shield layer 25 consists of copper.

The coating layer 26 can be fabricated by a biocompatible material, such as silicone or polyurethane. In one embodiment, the material of the coating layer 26 is polyurethane.

A working process of the pacemaker 100 acting on the heart of human being is described below. The electrode lead 20 is implanted into the heart of a human, with the bared part 40 used as electrode head contacting the heart. The pulse signals are generated by the pulse generator 10 and transmitted to the bared part 40 to stimulate the heart. A heartbeat frequency or a series of heartbeat frequencies can be sensed by detecting potential differences between the bared part 40 and the pulse generator 10. The potential differences are fed back to the pulse generator 10 to adjust the pulse signals to make the heart beat normally.

The carbon nanotubes have excellent mechanical strength and toughness. Accordingly, the carbon nanotube film 23 consisting of the carbon nanotubes have excellent mechanical strength and toughness. If the electrode lead 20 is stretched by a drawing force, the metal conductive core 22 will elongate along the stretching direction. The carbon nanotube film 23 wrapped around the metal conductive core 22 can prevent the metal conductive core 22 from breaking due to a friction force between the carbon nanotube film 23 and the metal conductive core 22. Therefore, the electrode lead 20 does not break easily under the same drawing force. In addition, the carbon nanotube film 23 has more strength and roughness than the metal conductive core 22. Thus, even if the metal conductive core 22 in the electrode lead 20 is broken, the carbon nanotube film 23 remains unchanged, and the carbon nanotube film 23 is still electrically conductive because the carbon nanotube film 23 is electrically connected to the metal conductive core 22. Therefore, the electrode lead 20 can still be electrically conductive. The mechanical strength and the toughness of the electrode lead 20 can be improved, and the lifespans of the electrode lead 20 and the pacemaker using the electrode lead 20 can be also improved.

The carbon nanotubes in the carbon nanotube film 23 extend substantially along the extending direction of the metal conductive core 22. The carbon nanotubes have good electrical conductivity along the extending direction of the carbon nanotubes because the carbon nanotube axial conductivity is excellent and the carbon nanotube axial conductive path is short. Therefore, the electrical conductivity of the electrode lead 20 can be improved. Thus, the sensitivity and the efficiency of the pacemaker 100 are improved.

Figure 6:
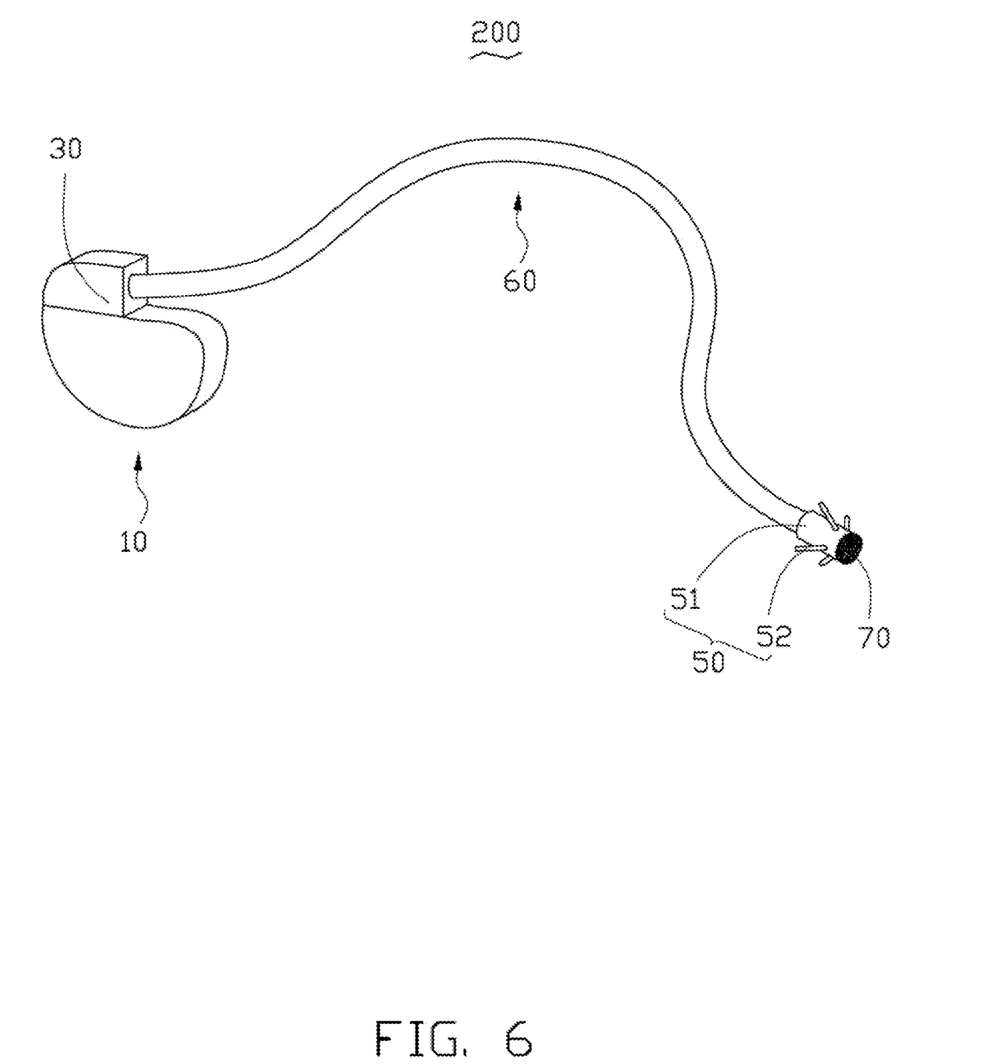
FIG. 6 shows a schematic view of one embodiment of a heart pacemaker.

Referring to FIG. 6, another embodiment of a pacemaker 200 is provided. The pacemaker 200 includes a pulse generator 10 and an electrode lead 60. A connector 30 is located at one end of the electrode lead 60. A bared part (not shown) is located at another end of the electrode lead 60.

The electrode lead 60 includes an electrode head 70 fixed on the bared part. The electrode head 70 is electrically connected with the electrode lead 60. Thus, the electrode head 70 can be used to transfer the pulse signals produced from the pulse generator 10 to the organ of the human body, to stimulate the organ of the human body.

A material of the electrode head 70 can be metal or alloy having an excellent conductivity, such as platinum-iridium alloy. A porous material to ensure biocompatibility can be coated on an outer surface of the electrode head 70. In addition, the porous material can increase the contact area between the electrode head 70 and the human body, thereby increasing the sensitivity and sensing efficiency of the pacemaker. The porous material can be activated carbon, carbon fiber, carbon nanotubes, or titanium-nitrogen alloy.

The electrode lead 60 can further include a fixture 50 located on one end of the electrode lead 60 being close to the electrode head 70. Thus, the fixture 50 can be opposite to and away from the connector 30. A material of the fixture 50 can be a polymer, such as polyurethane or silicon rubber. The fixture 50 can include a fixing ring 51 and a plurality of fixing wings 52. The fixing ring 51 can be a cylindrical structure. The plurality of fixing wings 52 can be rod-shaped. The plurality of fixing wings 52 forms a branch axis diverging from a center line or axis of the fixing ring 51, to form a barb structure. A diverging direction deviates from the extending direction of the electrode lead 20. An angle between the extending direction of each fixing wing 52 and the center line of the fixing ring 51 can be in a range from about 30 degrees to about 60 degrees. The fixture 50 can be fixed to the organ with the fixing wings 52 wrapped around by the fibrous tissue. The fixture 50 can also be a protrusion or helical structure as long as the electrode lead 20 can be tightly fixed to the organ by fibrous tissues.

Other characteristics of the pacemaker 200 are the same as those of the pacemaker 100.

It is to be understood that the above-described embodiment is intended to illustrate rather than limit the disclosure. Variations may be made to the embodiment without departing from the spirit of the disclosure as claimed. The above-described embodiments are intended to illustrate the scope of the disclosure and not restricted to the scope of the disclosure.

It is also to be understood that the above description and the claims drawn to a method may include some indication in reference to certain steps. However, the indication used is only to be viewed for identification purposes and not as a suggestion as to an order for the steps.

What is claimed is:

1. An electrode lead of a pacemaker, comprising:
    a metal conductive core defining an extending direction;
    a carbon nanotube film wrapped around an outer surface of the metal conductive core, the carbon nanotube film comprising a plurality of carbon nanotubes extending substantially along the extending direction of the metal conductive core, wherein the metal conductive core wrapped the carbon nanotube film is spirally twisted around to form a hollow spiral conductive structure;
    an insulated layer surrounding an outer surface of the hollow spiral conductive structure;
    a shield layer wound around the insulated layer; and
    a coating layer wrapped around the shield layer and comprising biocompatible material;
wherein one end of the hollow spiral conductive structure is exposed from the insulated layer, the shield layer, and the coating layer to form a bared part at a distal end of the electrode lead.

2. The electrode lead of claim 1, further comprising an electrode head electrically connected with the bared part.

3. The electrode lead of claim 2, further comprising a fixture located on one end of the electrode lead close to the electrode head, wherein the fixture is configured to fix the electrode lead to an organ in application.

4. The electrode lead of claim 3, wherein the fixture comprises a fixing ring and a plurality of fixing wings, the plurality of fixing wings forms a branch axis diverging from a center line of the fixing ring.

5. The electrode lead of claim 4, wherein an angle between an extending direction of each of the plurality of fixing wings and the center line of the fixing ring is in a range from about 30 degrees to about 60 degrees.

6. The electrode lead of claim 1, wherein the carbon nanotube film is adhered to the outer surface of the metal conductive core by van der Waals force.

7. The electrode lead of claim 1, further comprising an adhesive layer wherein the carbon nanotube film is adhered to the outer surface of the metal conductive core by the adhesive layer.

8. The electrode lead of claim 1, wherein the plurality of carbon nanotubes are joined end-to-end by van der Waals force along an axis direction of the plurality of carbon nanotubes.

9. The electrode lead of claim 1, wherein a material of the metal conductive core is selected from the group consisting of an alloy comprising of 35Co-35Ni-20Cr-10Mo and a weight percentage of titanium being about 1% or 0.01%, stainless steel, carbon fiber, tantalum, titanium, zirconium, niobium, titanium alloy, copper, silver, platinum, platinum-yttrium alloy, and platinum-palladium alloy.

10. The electrode lead of claim 1, further comprising a connector located at a proximal end the electrode lead.

11. The electrode lead of claim 1, wherein the hollow spiral conductive structure consists of the metal conductive core and the carbon nanotube film.

12. A pacemaker, comprising a pulse generator producing a pulse signal and an electrode lead transmitting the pulse signal, the electrode lead comprising:
a hollow spiral conductive structure comprising a metal conductive core and a carbon nanotube film wound around an outer surface of the metal conductive core, wherein the metal conductive core wrapped with the carbon nanotube film is spirally twisted around an axial of the hollow spiral conductive structure;
an insulated layer surrounding an outer surface of the hollow spiral conductive structure;
a shield layer winding around the insulated layer; and
a coating layer wrapped around the shield layer and comprising biocompatible material, wherein an end of the hollow spiral conductive structure is exposed out of the insulated layer, the shield layer and the coating layer to form a bared part at a distal end of the electrode lead.

13. The pacemaker of claim 12, wherein the electrode lead further comprises a fixture located on the end of the hollow spiral conductive structure being configured to fix the electrode lead in an organ.

14. The pacemaker of claim 12, wherein the hollow spiral conductive, the insulated layer, the shield layer, and the coating layer are coaxial.

15. The pacemaker of claim 12, wherein the carbon nanotubes film comprises a plurality of carbon nanotubes oriented along a extending direction of the metal conductive core.

16. The pacemaker of claim 15, wherein the plurality of carbon nanotubes is joined end to end along the extending direction.

17. The pacemaker of claim 12, further comprising a connector located at a proximal end the electrode lead, and the electrode lead is electrically connected to the pulse generator through the connector.

18. The pacemaker of claim 12, wherein the hollow spiral conductive structure consists of the metal conductive core and the carbon nanotube film.

19. The pacemaker of claim 12, wherein the carbon nanotube film is adhered to the outer surface of the metal conductive core by van der Waals force or an adhesive layer.

20. An electrode lead of a pacemaker, comprising:
a metal conductive core; and
a carbon nanotube film wrapped around an outer surface of the metal conductive core to form a conductive structure, wherein the carbon nanotube film comprises a plurality of carbon nanotubes joined end to end van der Waals force along an axis direction of the plurality of carbon nanotubes and oriented along the metal conductive core;
an insulated layer surrounding an outer surface of the conductive structure;
a shield layer wound around the insulated layer; and
a coating layer wrapped around the shield layer and comprising biocompatible material;
wherein one end of the conductive structure is exposed from the insulated layer, the shield layer, and the coating layer to form a bared part at a distal end of the electrode lead.

* * * * *